(12) United States Patent
Weisheit et al.

(10) Patent No.: US 6,713,275 B1
(45) Date of Patent: Mar. 30, 2004

(54) METHOD FOR DETERMINING ALKALINE PHOSPHATASE

(75) Inventors: Ralph Weisheit, Peissenberg (DE); Wolfgang Treiber, Weilheim (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/806,983

(22) PCT Filed: Oct. 5, 1999

(86) PCT No.: PCT/EP99/07366

§ 371 (c)(1), (2), (4) Date: Apr. 6, 2001

(87) PCT Pub. No.: WO00/22161

PCT Pub. Date: Apr. 20, 2000

(30) Foreign Application Priority Data

Oct. 8, 1998 (DE) .......................... 198 46 300

(51) Int. Cl.[7] ................................ C12Q 1/42
(52) U.S. Cl. .......................... 435/21; 436/15
(58) Field of Search .............. 435/4, 21, 967; 436/15, 164

(56) References Cited

U.S. PATENT DOCUMENTS

| | | | |
|---|---|---|---|
| 5,766,872 A | 6/1998 | Cybulski | 435/22 |
| 6,013,467 A * | 1/2000 | Siedel et al. | 435/25 |
| 6,207,459 B1 * | 3/2001 | Weisheit et al. | 436/66 |

FOREIGN PATENT DOCUMENTS

| | | | |
|---|---|---|---|
| EP | 0695805 A2 | 2/1996 | C12Q/1/32 |
| WO | WO97/45728 | 12/1997 | G01N/33/487 |
| WO | WO97/45732 * | 12/1997 | G01N/33/72 |
| WO | WO97/45733 | 12/1997 | G01N/33/52 |
| WO | WO 98/02570 * | 1/1998 | C12Q/1/26 |
| WO | WO98/02570 | 1/1998 | C12Q/1/40 |

OTHER PUBLICATIONS

Jay, D.W. and Provasek, D., "Characterization and Mathematical Correction of Hemolysis Interference in Selected Hitachi 717 Assays", Clinical Chemistry, 39(9), 1804–1810, 1993.*

Chance, J.J., Norris, E.J. and Kroll, M.H., "Mechanism of Interference of a Polymerized Hemoglobin Blood Substitute in an Alkaline Phosphates Method", Clinical Chemistry, 46(9), 1331–1337, 2000.*

* cited by examiner

Primary Examiner—Ralph Gitomer
(74) Attorney, Agent, or Firm—Brinks Hofer Gilson & Lione

(57) ABSTRACT

The invention concerns a method for the determination of alkaline phosphatase in a sample by optical measurement which is characterized in that a main measurement wavelength of 450±10 nm in combination with the rate blank procedure is used to eliminate haemoglobin interference, a method for eliminating interference by free haemoglobin or blood substitutes and the use of the combination of a main measurement wavelength with the rate blank procedure to eliminate interference by free haemoglobin or blood substitutes in the determination of alkaline phosphatase.

16 Claims, No Drawings

METHOD FOR DETERMINING ALKALINE PHOSPHATASE

This application is filed as a 371 application and claims priority to PCT/EP99/07366 filed Oct. 5, 1999, which claims priority to Germany 198 46 300.6 filed Oct 8, 1998.

BACKGROUND

The present invention concerns a method for the determination of alkaline phosphatase in a sample by optical measurement which is characterized in that a main measurement wavelength of 450±10 nm in combination with the rate blank method is used to eliminate haemoglobin interference, a method for eliminating interference by free haemoglobin or blood substitutes and the use of the combination of a main measurement wavelength with the rate blank method to eliminate interference by free haemoglobin or blood substitutes.

It is known that haemolysis considerably interferes with some diagnostic methods for the determination of analytes. Haemolysis is understood as any destruction of erythrocytes for example by mechanical, osmotic, chemical or enzymatic action on the cell membrane of the erythrocytes. As a result of haemolysis, the blood pigment haemoglobin (Hb) is released and can no longer be removed from a sample. The presence of haemoglobin is problematic because, on the one hand, the absorption spectrum of haemoglobin in some cases overlaps considerably with the spectra of the substances to be detected and indicators (chromogens) which can result in measuring errors in photometric tests. On the other hand, haemoglobin can also react chemically with sample components to form substances which can also result in false measurements.

Recently blood substitutes whose manufacture is based on haemoglobin are being used more and more frequently for therapeutic purposes for example after a large loss of blood. The haemoglobin in blood substitutes can be native or synthetic. Often Hb-like compounds are also used. In contrast to haemolysis in which there is usually a haemoglobin content of up to 500 mg/dl, the Hb content in blood serum or plasma may be more than 2000 mg/dl during treatment with blood substitutes. Hence interference in samples which contain blood substitutes is often considerably more pronounced than in haemolytic samples since the haemoglobin or the synthetic analogue is in a free form right from the beginning.

Interference by free haemoglobin is particularly serious in the photometric determination of alkaline phosphatase. The formation of 4-nitrophenol is measured at 405 to 415 nm (increase of absorbance) for the determination of alkaline phosphatase. Haemoglobin also absorbs at 415 nm. The presence of haemoglobin interferes with the determination of alkaline phosphatase in two respects: On the one hand the Hb spectrum changes in a time-dependent manner (increase of absorbance) in an alkaline medium, on the other hand, the photometer limit of the measuring instrument is reached above a certain Hb content.

Various methods have been published in the prior art to eliminate the spectral and chemical influence of haemoglobin on the analysis of serum or plasma samples.

Jay and Provasek describe in clin. Chem. 39/9, 1804–1810 (1993) that haemoglobin interference of the alkaline phosphatase determination is caused by a time-dependent change of the Hb spectrum. This interference can be eliminated by mathematical correction algorithms (determination of the Hb concentration in the sample and correction of the measured value for alkaline phosphatase by a certain amount that is equivalent to the measured amount of Hb).

Although the mathematical correction mentioned by Jay and Provasek eliminates the influence of Hb up to at least 800 mg/dl Hb, it is, however, not very user-friendly since it requires an additional measurement of the Hb content and subsequently an additional mathematical correction step.

Jay and Provasek (supra) describe a further method for eliminating interference by the so-called rate-blank measurement. The correction of haemolysis interference by rate-blank measurements is also described in EP-A-0 695 805, which is hereby incorporated by reference in its entirety. In this method the sample is subjected to a pre-reaction to determine the degree of haemolysis of the sample before the actual photometric determination of a component contained in the sample. The measured value obtained subsequently is then corrected by a value which has been determined by correlating the degree of haemolysis with the amount by which the interfering components contribute to the measuring error.

Hb interference can be eliminated by rate-blank measurements but only up to a Hb content of ca. 1200 mg/dl since the photometer limit is reached at higher Hb contents. This may be adequate for eliminating haemolysis interference but it is not sufficient at all for eliminating interference by blood substitutes.

Another method for eliminating haemoglobin interference was published for the determination of albumin (PCT application WO 97/45728) in which an elimination of haemoglobin interference was achieved by special combinations of main and secondary wavelengths. However, the wavelength combinations mentioned here cannot be used for the determination of alkaline phosphatase since a measuring sign al would no longer be obtained for 4-nitrophenol at these wavelengths.

The laid-open publication WO 97/45733 describes that interference by haemoglobin can be eliminated by using the secondary wavelengths 546 and 570 in individual UV tests. However, this method can only be used for enzymatic UV tests with a main measurement wavelength of 340 nm. Although a complete elimination of Hb interference can be achieved solely by the use of the secondary wavelengths 546 or 570 nm, this is not possible for enzymatic chromogenic tests such as the determination of alkaline phosphatase in which the main measurement wavelength is in the range of 415 nm.

The U.S. Pat. No. 5,766,872 mentions that a secondary wavelength of 577 nm reduces haemolysis interference in the amylase determination. However, the quoted measurement data show that there is already a significant deviation of the measured values of up to 8% at a Hb content of 500 mg/dl. This may be sufficient to eliminate haemolysis interference but it is probable that at higher Hb concentrations (such as those which occur during treatment with blood substitutes) this deviation of the measured values would become larger due to the use of a main measurement wavelength of ca. 415 nm and that there would no longer be an adequate elimination of Hb interference.

No method for the determination of alkaline phosphatase is known in the prior art which can also be carried out without interference in the presence of high concentrations of Hb such as those which occur in samples containing blood substitutes.

The object was therefore to develop an improved method for the determination of alkaline phosphatase in a sample which largely overcomes the disadvantages of the prior art. In particular it is intended to provide a simple and user-friendly method for eliminating interference by haemoglobin and by blood substitutes based on haemoglobin when determining alkaline phosphatase.

SUMMARY OF THE INVENTION

The object is achieved by a method described in more detail in the claims for the determination of alkaline phosphatase in a sample by optical measurement. The method is characterized in that 450±10 nm is used as a main measurement wavelength in combination with the rate blank procedure.

It surprisingly turned out that Hb interference of the determination of alkaline phosphatase can be effectively eliminated when the main wavelength is changed and the rate blank procedure is used. It is not sufficient for a satisfactory elimination of Hb interference to only change the main wavelength or only use the rate blank procedure.

DETAILED DESCRIPTION

Due to the absorption spectrum of 4-nitrophenol it is possible to measure alkaline phosphatase not only at 415 nm but also at 450±10 nm. Although the main measurement wavelength is then not in the usual absorption maximum of the detection reaction but on its flank, the measured signal obtained is nevertheless adequate for an exact determination of alkaline phosphatase.

The selection of the new main measurement wavelength of 450±10 nm already leads to a slight reduction of the haemoglobin interference, but a complete elimination of interference is surprisingly only obtained by combining the main wavelength of 450±10 nm with the rate blank procedure.

The method according to the invention enables interference of the alkaline phosphatase determination by haemoglobin or haemoglobin-like compounds to be eliminated for the first time in a simple manner up to a Hb content of at least 3000 mg/dl. The upper limit for the elimination of Hb interference is the limit determined by the performance of the photometer. Hence the method according to the invention can be expected to achieve a good elimination of interference up to 6500 mg/dl haemoglobin content.

In the rate blank procedure according to the invention the sample is subjected to a pre-reaction to determine the degree of haemolysis of the sample before the actual photometric determination of a component contained in the sample. The measured value for the component to be determined obtained subsequently is then corrected by a value which has been determined by correlating the degree of haemolysis with the amount by which the interfering components contribute to the measuring error. Use of the rate blank procedure per se to correct for haemolysis interference is described for example in EP-A-0 695 805 and by Jay and Provasek in Clin. Chem. 39/9, 1804–1810 (1993).

The secondary measurement wavelength used for the rate blank procedure is unimportant for the invention. Also the length of the time window for the measurement of the pre-reaction and the main reaction is not decisive. It has proven to be suitable to measure the absorbance change of the pre-reaction and main reaction over a time period of 1 to 4 minutes.

The method according to the invention is suitable for a determination of any samples in which free haemoglobin is present. The term free haemoglobin in the sense of the invention is used to distinguish it from haemoglobin which is present in intact erythrocytes. Examples of samples which contains free haemoglobin are haemolytic serum or plasma samples or samples which contain blood substitutes. Examples of blood substitutes that fall under the term free haemoglobin in the sense of the present invention are derivatized, polymerized, modified or cross-linked derivatives of haemoglobin in particular human haemoglobin or bovine haemoglobin e.g. DCL haemoglobin (diaspirin-crosslinked haemoglobin) or recombinantly produced haemoglobin.

The invention also concerns a method for eliminating interference caused by free haemoglobin in a method for determining alkaline phosphatase. The method is characterized in that a main measurement wavelength of 450±10 nm in combination with the rate blank procedure is used.

A further subject matter of the invention is the use of a main measurement wavelength of 450±10 nm in combination with the rate blank procedure to eliminate interference by free haemoglobin or by blood substitutes manufactured from haemoglobin in a method for determining alkaline phosphatase.

The invention is elucidated by the following example.

EXAMPLE a) Preparation of samples Containing Haemoglobin

A solution containing Hb was added to a part of a serum pool to yield a Hb content of at least 3000 mg/dl. Another part of the same serum pool of the same volume was admixed with an equivalent amount of NaCl solution (154 mmol/l). Both parts were subsequently mixed with one another in different ratios to obtain a Hb concentration series of 11 samples with no Hb in the lowest sample and at least 3000 mg/dl Hb in the highest sample.

b) Determination of Alkaline Phosphatase According to the SFBC Method

Determination according to the recommendation to the Société Francaise de Biologie Clinique according to Ann. Biol. Clin. Vol. 35, 271 (1977).

The determination of alkaline phosphatase was carried out on a Boehringer Mannheim/Hitachi 911 analyzer.

The following reagents were used:

reagent 1: 930 mmol/l2-amino-2-methyl-1-propanol buffer pH 10.5; 1.03 mmol/l magnesium aspartate reagent 2: 930 mmol/l2-amino-2-methyl-1-propanol buffer, pH 10.5; 1.03 mmol/l magnesium aspartate; 98 mmol/l 4-nitrophenyl phosphate The test procedure was as follows: 250 µl reagent 1 was added to 11 µl sample and after 5 min 50 µl reagent 2 was added. For the comparative measurements the analyte was determined after a further 50 sec during which the change in absorbance was measured during the subsequent 4 min. Combinations of the following main measurement wavelengths ($\lambda_1$) and secondary measurement wavelengths ($\lambda_2$) were used for the measurement: $\lambda_1/\lambda_2$=415/660 nm (previous instrument settings), 415/570 nm and 450/660 nm (comparison). Furthermore alkaline phosphatase was determined by the rate blank measurement mentioned by Jay and Provasek as a further comparison (referred to as 415/660 nm RB).

The measurement wavelength combination $\lambda_1/\lambda_2$=450/660 nm was used to determine the analyte according to the invention. For the rate blank measurement the change in absorbance of the pre-reaction was measured in the period 3.0–4.9 min after addition of reagent 1 to the sample and the change in absorbance of the main reaction was measured in the period 7.9–9.8 min after addition of reagent 1 in the sample. This corresponds to the measurement points [10]–[16] and [25]–[31] on the Boehringer Mannheim/Hitachi 911 analyzer. The result is shown in the column labelled "450/660 nm RB".

The results of the measurement according to the invention as well as the comparison measurements are shown in the following table 1. It can be seen that the use of the inventive combination of the new main wavelength of 450 nm and the rate blank procedure considerably reduces, interference by blood substitutes containing Hb compared to the other measurement wavlength combinations or compared to the rate blank measurement at the main wavelength of 415 nm.

TABLE 1

Measured content of alkaline phosphatase at 37° C. in U/l

| Hb content* [mg/dl] | 415/660 nm | 415/570 nm | 450/660 nm | 415/660 nm RB | 450/660 nm RB |
|---|---|---|---|---|---|
| 0 | 42 | 42 | 42 | 42 | 42 |
| 300 | 32 | 32 | 35 | 44 | 43 |
| 600 | 22 | 24 | 29 | 46 | 44 |
| 900 | 14 | 16 | 24 | 46 | 46 |
| 1200 | 8 | 11 | 22 | 44 | 45 |
| 1500 | 3 | 7 | 19 | 5 | 47 |
| 1800 | −2 | 2 | 17 | 0 | 47 |
| 2100 | −2 | 3 | 17 | 0 | 48 |
| 2400 | −2 | 3 | 15 | 1 | 50 |
| 2700 | −1 | 3 | 16 | 0 | 49 |
| 3000 | −2 | 3 | 19 | 1 | 51 |

*in this case a cross-linked haemoglobin was used.

What is claimed is:

1. A method of eliminating interference by hemoglobin in the determination of alkaline phosphatase in a sample, comprising:
   determination a first optical measurement of said sample at 450±10 nm;
   adding 4-nitrophenyl phosphate to said sample;
   determining a second optical measurement of said sample at 450±10 nm; and
   correcting the second optical measurement with the first optical measurement.

2. The method of claim 1, wherein the optical measurement comprises an absorbance determination.

3. The method of claim 1, wherein said sample comprises a plasma or serum sample.

4. The method of claim 1, wherein said sample comprises a blood substitute.

5. The method of claim 4, wherein the blood substitute comprises derivatized hemoglobin, polymerized hemoglobin, modified hemoglobin, or cross-linked hemoglobin.

6. The method of claim 4, wherein the blood substitute comprises human hemoglobin or bovine hemoglobin.

7. The method of claim 4, wherein the blood substitute comprises a recombinantly produced hemoglobin.

8. The method of claim 4, wherein the blood substitute comprises diaspirin-crosslinked hemoglobin.

9. The method of claim 1, wherein the step of determining a first optical measurement is conducted over a period of time of between about 1 and 4 minutes.

10. The method of claim 1, wherein said sample has a hemoglobin concentration of up to about 3000 mg/dl.

11. The method of claim 1, wherein said sample has a hemoglobin concentration of up to about 6500 mg/dl.

12. A method of determining a level of alkaline phosphatase in a sample containing 4-nitrophenyl phosphate, the method comprising:
   determining an optical measurement of said sample at 450±10 nm; and
   correcting the optical measurement by combining the optical measurement with a correction factor that represents a correlation between a degree of hemolysis of said sample and a level of interference due to hemoglobin present in said sample.

13. The method of claim 12, wherein the first optical measurement is determined in a pre-reaction.

14. The method of claim 12, wherein said sample comprises a plasma or serum sample.

15. The method of claim 12, wherein said sample comprises human hemoglobin or a blood substitute.

16. A method of determining a level of alkaline phosphatase in a sample, comprising:
   measuring a first change in absorbance of said sample at 450±10 nm;
   adding 4-nitrophenyl phosphate to said sample;
   measuring a second change in absorbance of said sample at 450±10 nm; and
   correcting the first change in absorbance with the second change in absorbance.

* * * * *

UNITED STATES PATENT AND TRADEMARK OFFICE
CERTIFICATE OF CORRECTION

PATENT NO. : 6,713,275 B1
DATED : March 30, 2004
INVENTOR(S) : Ralph Weisheit et al.

It is certified that error appears in the above-identified patent and that said Letters Patent is hereby corrected as shown below:

Title Page,
Item [56], References Cited, OTHER PUBLICATIONS,
"Chance, J.J.," reference, delete "Phosphates" and substitute -- Phosphatase -- in its place.
Item [57], ABSTRACT,
Lines 5, 6, and 9 delete "haemoglobin" and substitute -- hemoglobin -- in its place (all occurrences).

Column 6,
Line 8, delete "recombinantly produced" and substitute -- recombinantly-produced -- in its place.
Lines 18 to 27, delete and substitute the following in its place.
    -- A method of determining a level of alkaline phosphatase in a sample, the method comprising:
determining a first optical measurement of said sample at 450 ± 10 nm that represents a correlation between the amount of hemoglobin in the sample and the interference due to the hemoglobin; and
adding 4-nitrophenyl phosphate to said sample;
determining a second optical measurement of said sample at
450 ± 10 nm;
correcting the second optical measurement with the first optical measurement. --

Line 34, after claim 15, insert the following.
-- 16. The method of claim 12, wherein the hemoglobin comprises natural, synthetic, or recombinantly-produced hemoglobin. --

UNITED STATES PATENT AND TRADEMARK OFFICE
CERTIFICATE OF CORRECTION

PATENT NO. : 6,713,275 B1
DATED : March 30, 2004
INVENTOR(S) : Ralph Weisheit et al.

It is certified that error appears in the above-identified patent and that said Letters Patent is hereby corrected as shown below:

Column 6 (cont'd),
Renumber claim 16 as claim 17.

Signed and Sealed this

Twenty-ninth Day of March, 2005

JON W. DUDAS
*Director of the United States Patent and Trademark Office*